United States Patent [19]

Furnadjiev et al.

[11] 4,057,806
[45] Nov. 8, 1977

[54] APPARATUS FOR ANALYZING MOVEMENTS OF AN ANIMATE OR INANIMATE OBJECT

[75] Inventors: Vassil Lazarov Furnadjiev, Sofia; Boris Krestanov Samardjiev, Plovdiv, both of Bulgaria

[73] Assignee: CS na BSFS, Sofia, Bulgaria

[21] Appl. No.: 702,186

[22] Filed: July 2, 1976

[30] Foreign Application Priority Data

July 2, 1975    Bulgaria .................................. 30438

[51] Int. Cl.² ........................... G01D 5/02; G01D 9/30
[52] U.S. Cl. ................................. 346/33 R; 33/1 M; 272/123; 346/33 M; 346/49; 346/114
[58] Field of Search ................. 346/33 R, 33 M, 114, 346/49, 30; 73/379; 33/1 M, 18 B; 272/123, 122, DIG. 5

[56] References Cited

U.S. PATENT DOCUMENTS

| 3,370,296 | 2/1968 | Greenberg | 346/33 R X |
| 3,832,781 | 1/1973 | Flagge | 346/33 R X |

*Primary Examiner*—Joseph W. Hartary

[57] ABSTRACT

An arrangement is described for rapidly and accurately analyzing the movements of a barbell or other weight. The object is positioned in a suitable holder, which is connected by means of a pair of strands to the periphery of a first disc secured to a torsion-biased shaft. The strands extend, intermediate their ends, through opposed ends of the crosspiece of a T-shaped pendulum whose central arm is secured at its free end to a second disc, such second disc being in turn secured to a splined front end of the shaft. A pair of internally toothed racks are carried by the second disc for toothed engagement with the splined end of the shaft, with the racks being confined for movement in mutually perpendicular directions to resolve the motion of the holder and thereby of the object into orthogonal planes. Facilities are provided for recording the separate movements of the first and second racks along a common first coordinate of a recording medium as the medium is advanced along the other coordinate.

6 Claims, 5 Drawing Figures

APPARATUS FOR ANALYZING MOVEMENTS OF AN ANIMATE OR INANIMATE OBJECT

BACKGROUND OF THE INVENTION

The invention relates to arrangements for analyzing the movement of a prescribed object, particularly for athletic applications.

In one known arrangement for measuring the trajectory of a barbell or other weight handled by a weightlifter during training or actual competition, the vertical component of the movement is detected by coupling the object to a torsioned shaft having disposed thereon a disc which carries a toothed rack. Strands extending from a holder in engagement with the moving object are passed through opposite ends of a depending crossarm on a T-shaped pendulum that is affixed to the disc, whereby the movement of the object causes the pendulum to rotate the shaft; as a result, a splined front end of the shaft is effective to position the rack carried by the disc by an amount proportional to the vertical movement of the object.

The main advantage of such known scheme is its lack of flexibility, since by being confined to the measurement of vertical movements of the object, a complete study of the spatial or velocity characteristics of the weight and/or the athelete is inhibited.

SUMMARY OF THE INVENTION

These disadvantages are overcome with an improved motion analyzing arrangement of the general type indicated above, wherein the motion of an object (e.g., a weight or the athlete positioning the weight) can be resolved into several components for study and evaluation. In an illustrative embodiment, a second rack is carried by the front disc on the shaft for mutually perpendicular movement relative to the first rack. Such second rack is, like the first rack, disposed in toothed engagement with the splined front end of the shaft.

A pair of auxiliary strands extend from first ends of the first and second racks to first ends of a pair of linear biasing means whose opposite ends are secured to a fixed point. The so-biased auxiliary strands are affixed to a pair of indicia marking means, which are guided for movement along a first coordinate of a two-coordinate marking medium.

The movement of the indicia marking means accurately tracks the movement of the corresponding ends of the associated racks, which in turn are positioned in accordance with mutually orthogonal components of movement of the object. The other coordinate of the recording medium may be represented as a time base by which the medium is swept past the marking means, either continuously or incrementally.

As an additional feature of the invention, a pair of magnetic tapes are carried by the auxiliary strands for movement past a fixed pair of magnetic heads. Each of the tapes exhibits a plurality of uniformly spaced magnetic strips, which cause the generation of voltage pulses by the associated heads as the tape moves past the head in one of its two opposite directions. The direction of movement of the tape is detected by the closure of one of two associated pairs of contacts, which are closed upon the commencement of movement of the tape in a prescribed one of its two opposite directions.

Preferably, the main strands extending from the object holder are passed through opposed ends of the crossarm of the T-shaped pendulum and are secured to the periphery of an auxiliary disc secured to the shaft behind the rack-carrying disc.

BRIEF DESCRIPTION OF THE DRAWING

The invention is further set forth in the following detailed description taken in conjunction with the appended drawing, in which:

FIG. 4b is a series of curves representing the outputs of certain magnetic heads and contact pairs illustrated in FIG. 2 and corresponding to the information contained on the graph of FIG. 4a.

DETAILED DESCRIPTION

Figure 1:
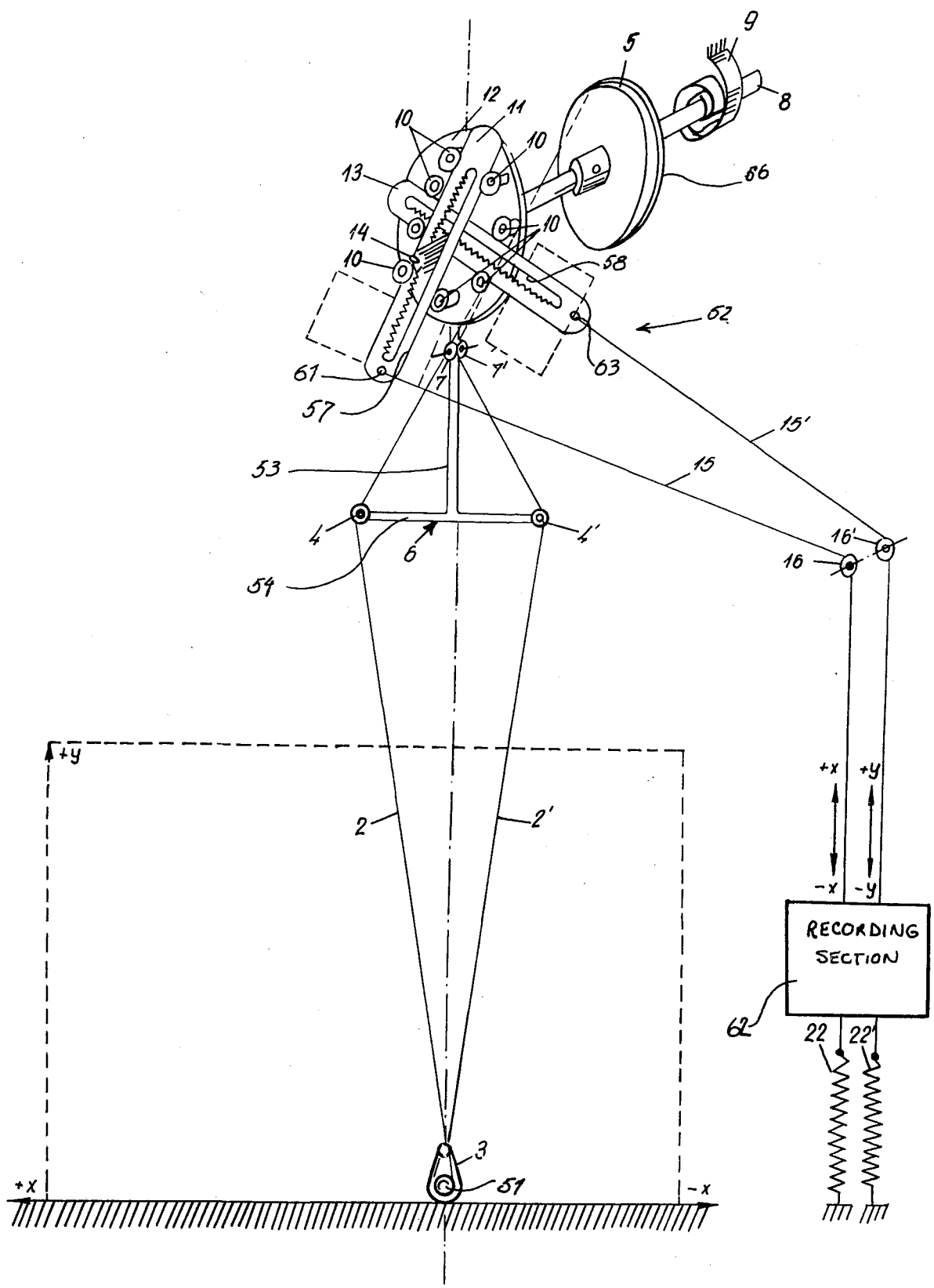
FIG. 1 is a perspective view of an embodiment of movement-analyzing apparatus constructed in accordance with the invention.

Referring now to the drawing, the numeral 51 represents an object, such as a barbell, shotput or other weight, whose path of movement during lifting by an athlete is to be measured.

The object 51 is carried in a suitable holder 3 that is associated with the measuring apparatus of the invention, represented at 52. The holder 3 is connected to the remainder of the measuring apparatus by means of a pair of strands 2, 2' in the manner described below.

The arrangement 52 includes an elongated shaft 8, whose front end exhibits a splined outer surface 14. A torsion spring 9 extends between the shaft 8 and a suitable fixed point for supporting the shaft 8 for bi-directional rotation about its axis, such torsion spring serving to continually load the shaft.

A disc 12 is fixedly supported on the splined front end 14 of the shaft 8. The disc 12 carries a T-shaped pendulum 6; in particular, the free end of a central arm 53 of the pendulum is affixed to the disc 12, such central arm terminating in a crossarm 54 whose opposed ends carry rollers 4, 4'. Because of the rigid connection of the pendulum, the disc 12 and the shaft, a movement of the pendulum 6 in the manner described below will be effective to rotate the shaft 8 and the disc 12.

An auxiliary disc 5 bearing a grooved peripheral edge 56 is fixedly supported on the shaft 8 in axially spaced relation to and rearwardly of the disc 12.

The strands 2, 2' extending from the holder 3 are routed around the rollers 4, 4' on the pendulum crosspiece 54, and then through a pair of rollers 7, 7' on the pendulum central arm 53 to be received in the grooved periphery 56 of the disc 5.

A plurality of rollers 10, 10 are rotatably mounted on the front face of the disc 12. In the arrangement shown, eight of the rollers are provided. Four of the eight rollers are situated to slidably suport a first rack 11, which has an internally toothed cutout 57 for engagement with the splined outer surface 14 of the shaft 8. Thus, when the shaft 8 rotates to correspondingly rotate the spline 14, the rack 11 is moved linearly in the confined direction dictated by the associated guide rollers 10. The degree of movement of such rack 11 is proportional to the rotational movement of the shaft.

The remaining four guide rollers 10 disposed on the disc 12 are situated to guide a second rack 13, which is disposed perpendicular to the first rack 11 and which has an internally toothed region 58 engaged by the spline 14 on the shaft 8.

The co-action of the mutually perpendicular racks 11 and 12 is effective to resolve a movement of the object 51 into two perpendicular coordinates of which the coordinate represented by the path of movement of the rack 11 is proportional to the component of movement of th object 51 along the horizontal (X) axis as viewed in FIG. 1; in like manner, displacements of the rack 13 along its constrained path of movement represents the component of motion of the object 51 along a vertical direction (Y) as viewed in FIG. 1.

In order to record the movements of the racks 11 and 13 for further analysis and utilization, the movements of the racks are respectively converted into indicia suitable for permanent tangible recording.

For this purpose, a first auxiliary strand 15 extends from a first end 61 of the rack 11, and after being routed around a first guide roller 16 is passed through a recording section indicated generally at 62, and terminates at an upper end of a linear biasing spring 22, whose lower end is attached to a fixed point. The biasing spring 22 is effective to maintain a positive load on the strand 15, and to avoid slack in the measurement. In like manner, a second auxiliary strand 15' extends from an end 63 of the other rack 13, and after being routed around a second guide roller 16' is extended through the recording section 62 to an upper end of a second linear biasing spring 22'; the other end of the spring 22' is connected to the fixed point for the purpose just indicated.

Figure 2:
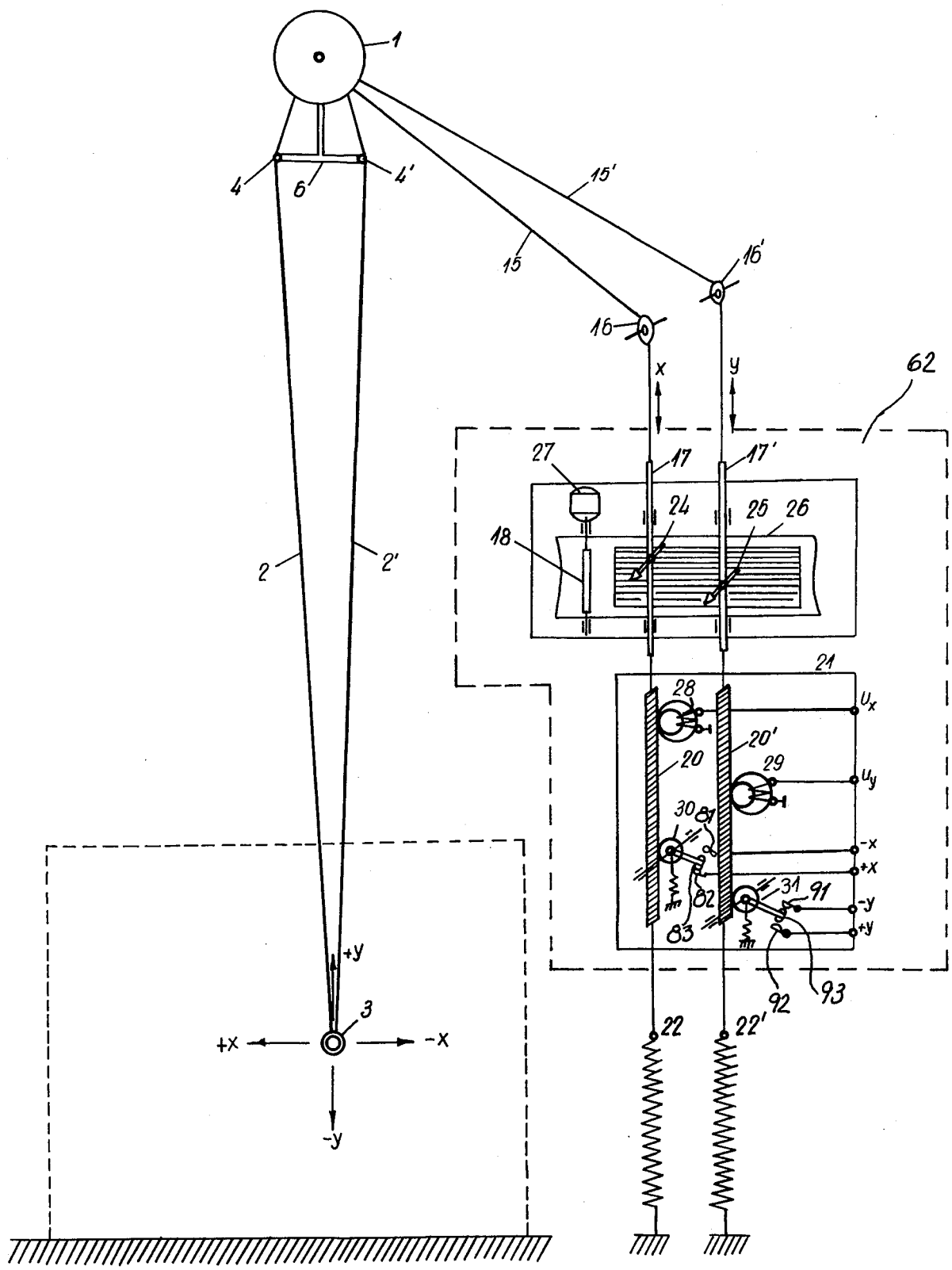
FIG. 2 is a representation of the arrangement of FIG. 1, illustrating additional details of the recording facilities associated therewith.

An illustrative embodiment of the recording section 62 is illustrated in FIG. 2. A pair of guides 17, 17' are inserted in the respective strands 15, 15' for essentially frictionless reciprocation over a recording medium, illustratively, an X—Y chart 26. A pair of pens 24, 25 are individually affixed to the guides 17, 17', the points of such pens being normally in contact with the chart 26 for marking indicia on the chart as the guides 17, 17', and thus the ends of the racks 11, 13, are moved proportional to the X—Y motion of the object being measured.

As shown in FIG. 2, the pens 24 and 25 are each adapted to mark the associated indicia along a given coordinate (e.g., a Y axis) of the chart 26. A perpendicular coordinate of the chart 26, e.g., an X or time axis, is instrumented by driving the tape in a direction perpendicular to the direction of movement of the pens, e.g., by means of a roller 18 affixed to a suitable drive motor 27.

With such arrangement, the amplitude-time trace registered by the pen 24 is proportional to the "X" component of motion of the object 51, while the parallel record formed by the pen 25 is indicative of the "Y" motion. This is exemplified in the chart trace of FIG. 4a, which results when the object defines a purely circular motion in a vertical plane. In this case, the record traced out by the "X" pen 24 as a function of time will be represented by a curve 71, while the record traced out by the "Y" pen 25 is represented by the curve 72.

An additional portion of the recording section 62 of FIG. 2 includes a magnetic transducer 21. The transducer 21 includes a pair of magnetic tapes 20, 20' which are individually affixed to the auxiliary strands 15, 15' and thereby move integrally with the guides 17, 17'.

Figure 4A:
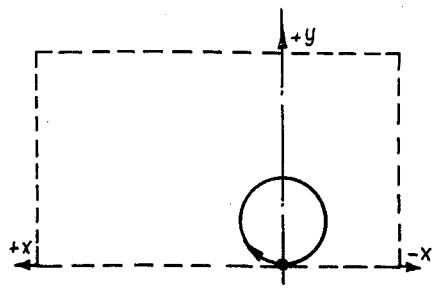
FIG. 4a is a graph of a record, formed with the recording apparatus of FIG. 2, of the analyzed motion of an object which is measured with the arrangement of FIG. 1.
Figure 4B:
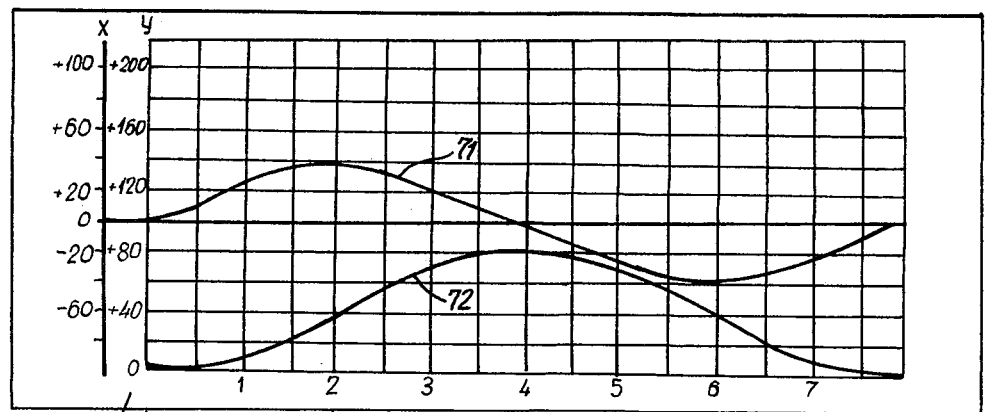
Figure 4B:
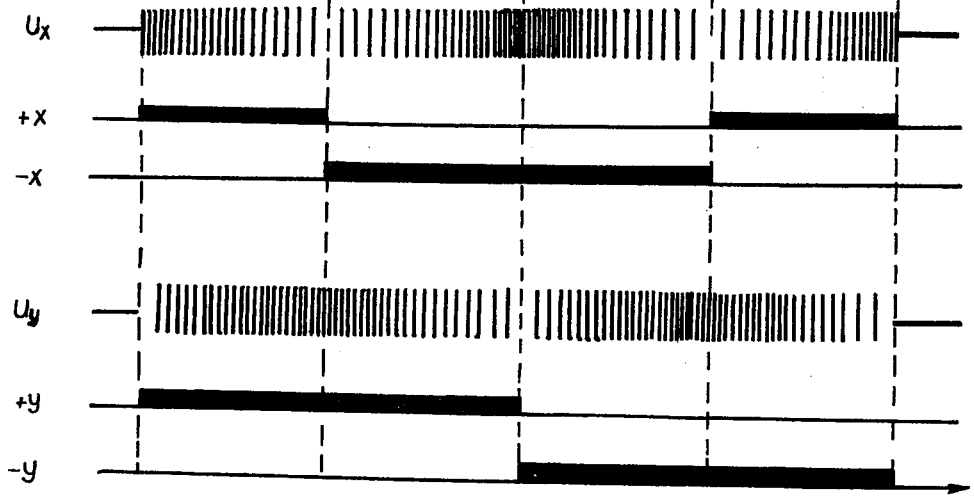

Each of the tapes 20, 20' have magnetic indicia uniformly spaced thereon, such indicia serving to generate, in a pair of stationary magnetic heads 28, 29 associated with the tapes as shown, voltage pulses (denoted $V_x$ and $V_y$) each time one of the indicia on the correponding tape passes the head. FIG. 4b, drawn to the same time scale as the X—Y plot of FIG. 4a, shows a typical pattern of pulses generated by each of the heads 28 and 29 in response to the above-mentioned circular motion of the object 51.

A contact arrangement 30 is also associated with the tape 20 for detecting and outpulsing signals representing changes of direction of the object 51 in the horizontal plane. For this purpose, the contact arrangement 30 includes a pair of fixed contacts 81 and 82 and an intervening movable contact 83. In the scheme shown, the commencement of movement of the tape 20 in one of its two opposite directions causes the closure of the contacts 82, 83, thereby yielding a "+X" signal. Such signal lasts as long as the tape 20 proceeds in its original direction. Upon a reversal of the direction of the tape, the movable contact 83 is transferred over to the other fixed contact 81, thereby generating a "—X" signal.

In an exactly analogous manner, a contact arrangement 31, including a pair of fixed contacts 91, 92 and a movable contact 93, cooperates with the tape 20'. Accordingly, commencement of the tape 20' in one direction causes a closure of the contacts 92, 93 to yield a "+Y" signal, while commencement of movement of such tape in the opposite direction causes closure of the contacts 91, 93 to yield a "—Y" signal.

The signals generated by the respective contact sets 30, 31 for the case where the object 51 defines a circular motion as indicated above, is also shown in FIG. 4b.

The motor 27 may be embodied as a stepping switch which can be incremented in mutually opposite directions. If such a motor is employed, it may be incremented, for certain applications, by applying thereto successive pulses from one of the outputs of the magnetic transducer 21. It will be understood that many other types of time bases for the X-Y plot of the chart 26 can also be devised, depending on the specific application envisioned.

Figure 3:
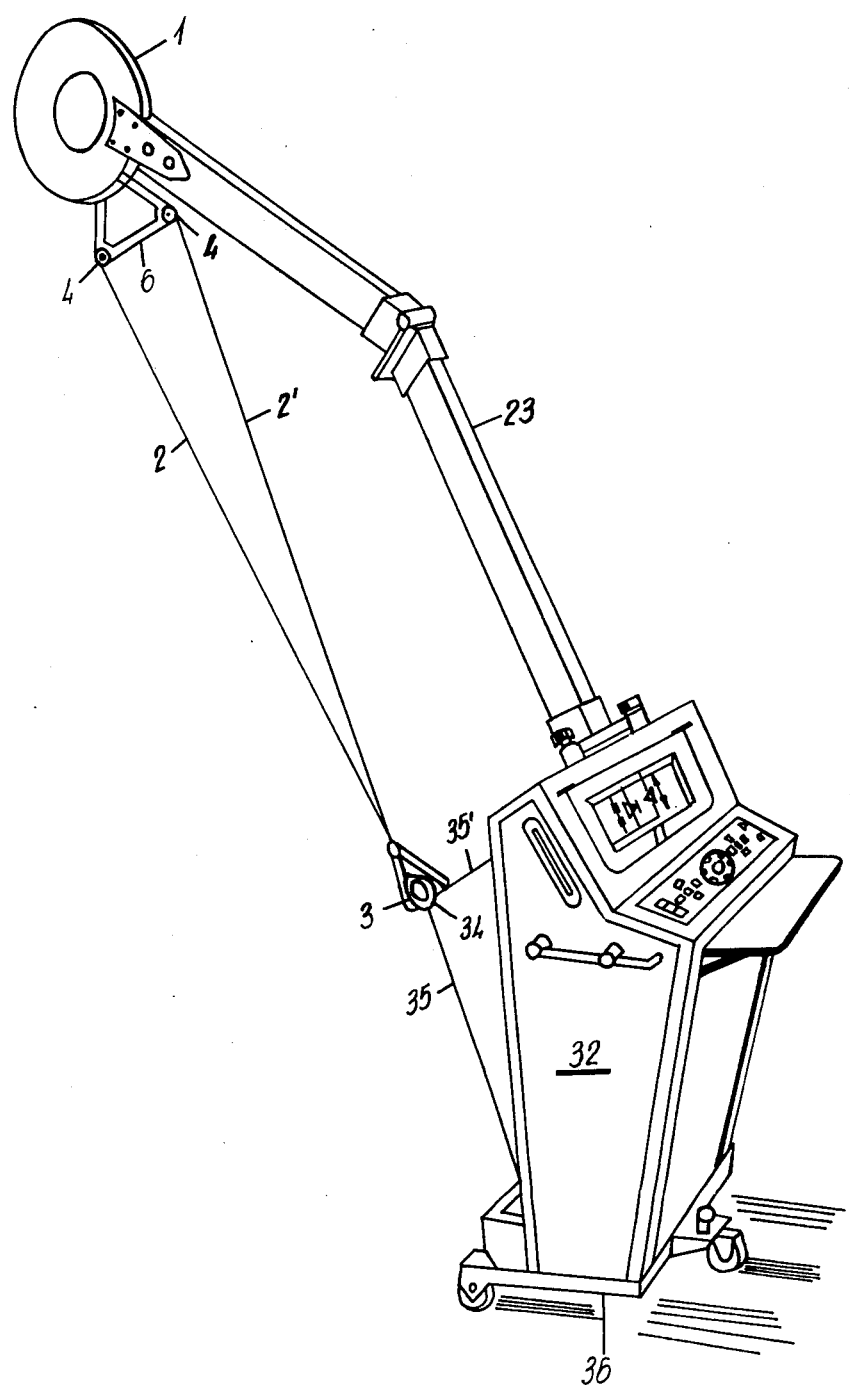
FIG. 3 is a perspective view illustrating the combination of a housed arrangement similar to that of FIGS. 1-2 with a control and monitoring console.

In the arrangement of FIG. 3, the components associated with the shaft 8 (including the spring 9, the grooved disc 5, and the rack-bearing disc 12) may be confined within a suitable housing 1. Such housing 1, in turn, is connected to a hinged conduit 23, which houses the auxiliary strands 15, 15'. The recording section 62 is housed within a suitable console unit 32, which is supported on a wheeled base 36.

In order to calibrate the chart 26 and the remainder of the recording apparatus, the console 32 may carry a test load 34, which prior to measurement of the main object 51 may be secured to the holder 3 and adjusted in position, as by strands 35, 35', until the measurement apparatus of the console attains a desired zero reference position. In such case, the strands 35, 35' may be associated with the pens 24, 25 on the recording section of the console. Following such calibration, the pens are secured in position, and the holder 3 is removed from the test load 35 and attached to the main object 51 for the main measurement described above.

In the foregoing, an illustrative arrangement of the invention has been described. Many variations and modifications will now occur to those skilled in the art. It is accordingly desired that the scope of the appended claims not be limited to the specific disclosure herein contained.

What is claimed is:

1. In an apparatus for analyzing movements of a prescribed object, a holder for carrying the object, a shaft having front and rear ends and exhibiting a splined outer surface at its front end, torsion-applying means coupled to the shaft and supporting the shaft for bidirectional rotation under load about a first axis, a first disc fixedly supported on the shaft, a second disc fixedly supported on the shaft forwardly of the first disc and disposed around the forward splined end of the shaft, a T-shaped element having a central arm secured to and extending outwardly from the second disc, first and second strands individually extending from a prescribed point of the holder to the periphery of the first disc through the respective ends of the crossarm of the T-shaped element for effecting a rotation of the shaft upon a movement of the holder, first and second racks each having internal teeth, means carried by the second disc for individually supporting the first and second racks in toothed engagement with the splined front end of the shaft for movement in mutually perpendicular directions, and recording means associated with the first and second racks for generating separate indicia instantaneously indicative of the then-occurring movements of the respective racks.

2. Apparatus as defined in claim 1, in which the recording means comprises, in combination, a record medium having first and second coordinates, first and second marking means separately supported for movement along the first coordinate of the medium, first means coupling the first rack to the first marking means to move the first marking means along the first coordinate by an amount proportional and in a direction corresponding to the movement of the first rack, and second means coupling the second rack to the second marking means to move the second marking means along the first coordinate by an amount proportional and in a direction corresponding to the movement of the second rack.

3. Apparatus as defined in claim 2, in which the first and second moving means individually comprise, in combination, first and second linear biasing means each having a first end connectable to a fixed point, a third strand extending between an end of the first rack and the opposite end of the first linear biasing means, and a fourth strand extending between and end of the second rack and the opposite end of the second linear biasing means, the first marking means being affixed to the third strand and the second marking means being affixed to the fourth strand.

4. Apparatus as defined in claim 2, further comprising means for advancing the medium along the second coordinate relative to the first and second marking means.

5. Apparatus as defined in claim 2, further comprising first and second tapes individually affixed to the first and second moving means for movement therewith, each tape carrying a plurality of uniformly spaced magnetic indicia thereon, and first and second magnetic heads individually disposed in magnetic coupling relation to the first and second tapes for generating a voltage pulse each time an indicia of the associated tape moves past the head.

6. Apparatus as defined in claim 2, further comprising first and second fixed contacts and a third movable contact each associated with each of the first and second tapes, means operable upon the commencement of movement of the associated tape in a first direction for moving the third contact into engagement with the first contact, and means operable upon the commencement of movement of the associated tape in the opposite direction for moving the third contact into engagement with the second contact.

* * * * *